United States Patent [19]

Norman

[11] 4,335,208

[45] Jun. 15, 1982

[54] SACCHARIFICATION OF STARCH HYDROLYSATES

[75] Inventor: Barrie E. Norman, Farum, Denmark

[73] Assignee: Novo Industri A/S, Denmark

[21] Appl. No.: 129,314

[22] Filed: Mar. 11, 1980

[51] Int. Cl.³ .................... C12P 19/16; C12P 19/20; C12R 1/38; C12R 1/685
[52] U.S. Cl. ............................ 435/96; 435/98; 435/874; 435/917
[58] Field of Search ............... 435/96, 42, 72, 98, 435/99, 105, 205, 210, 874, 917; 127/29

[56] References Cited

U.S. PATENT DOCUMENTS

| | | | |
|---|---|---|---|
| 3,560,345 | 2/1971 | Yokobayashi et al. | 435/210 |
| 3,630,844 | 12/1971 | Hurst | 435/96 |
| 3,692,580 | 9/1972 | Hirao et al. | 435/98 |
| 3,897,305 | 7/1975 | Hurst | 435/96 |
| 4,017,363 | 4/1977 | McMullen et al. | 435/96 |

*Primary Examiner*—Raymond N. Jones
*Assistant Examiner*—Elizabeth J. Curtin
*Attorney, Agent, or Firm*—Fidelman, Wolffe & Waldron

[57] ABSTRACT

Saccharifying starch hydrolysate to a high DX glucose syrup at pH 3–5 by the enzyme mixture of a glucoamylase and an acidophilic iso-amylase. A lower dosage level than the heretofore conventional glucoamylase dosage may be employed and higher DX glucose syrups can be obtained.

8 Claims, 2 Drawing Figures

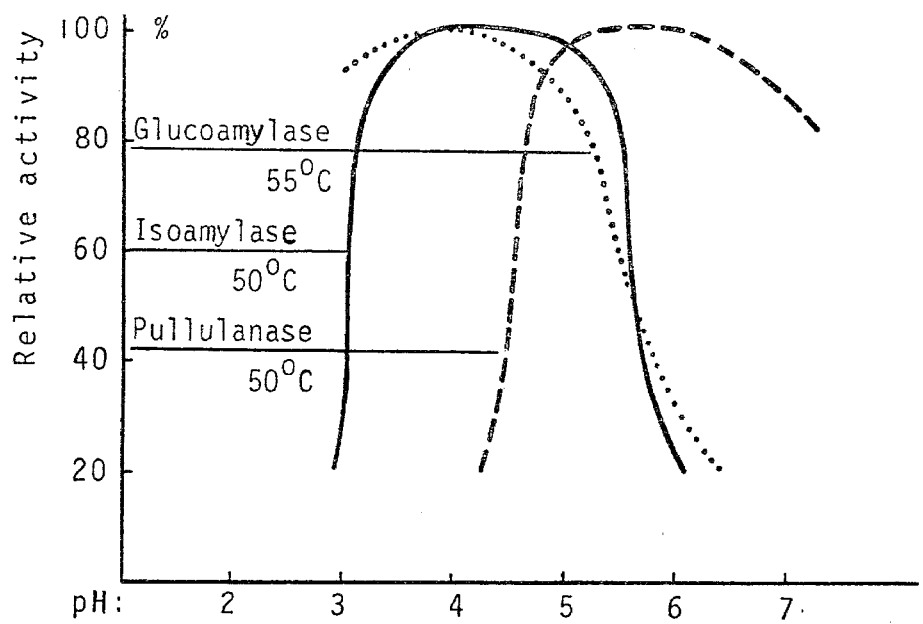
FIG. 1 The relative activity versus pH for glucoamylase (A. niger), isoamylase (Ps. amyloderamosa) and pullulanase (K. pneumoniae).
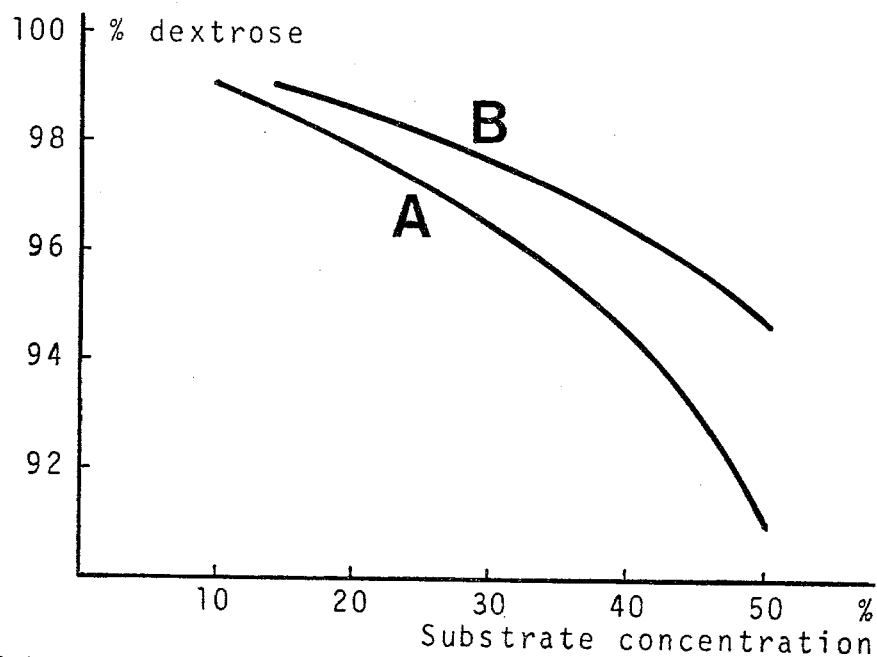
FIG. 2 The variation in maximum DX with substrate concentration.
Curve A: Standard saccharification (60°C; pH 4.0-4.5; 0.225 AG units/g DS).
Curve B: Isoamylase/glucoamylase saccharification (50°C; pH 4.0; 0.075 AG units/g DS and 200 IA units/g DS).

SACCHARIFICATION OF STARCH HYDROLYSATES

INTRODUCTION

This invention relates to the saccharification of starch hydrolysates.

The object of this invention is to provide a saccharification process productive of syrups with a higher dextrose (D-glucose) content than have been obtained heretofore from relatively concentrated starch hydrolysates, e.g., of more than about 30% solids by weight.

A second object of this invention is to reduce the dosage of glucoamylase required to saccharify maltodextrin solutions.

BACKGROUND OF THE INVENTION

Sugars from starch, in the form of concentrated dextrose syrups, are being produced at the rate of several million tons per annum as of the date hereof by a two stage enzyme catalyzed process: (1) liquefaction of the solid starch with an alpha-amylase, then (2) saccharification of the resulting starch hydrolysate with a glucoamylase. Much of the dextrose syrup produced commercially is then enzymatically isomerized to a dextrose/fructose mixture known as isosyrup.

The saccharification stage to which this invention is directed has long been recognized to be deficient in certain regards. In particular, the glucoamylases available to the art catalyze both saccharification and dextrose reversion reactions e.g., of dextrose into isomaltose. Existence of reversion reactions has limited the saccharification of starch hydrolysates into dextrose to not more than about 96% by wt. of dextrose on dry solids basis (hereinafter termed DX) in syrups having at least 30% solids by wt. In an effort to further increase the DX value the art has suggested employment of debranching enzymes (along with the glucoamylase) so as to hydrolyze more efficiently the branched chain oligosaccharides (containing 1,6-alpha-glucosidic bonds) present in the starch hydrolysate. For greater detail on the place of debranching enzymes in maltodextrin saccharification, reference is made to Allen et al. "Technology and Use of Debranching Enzymes," *Food Technology*, May 1975, pp. 70-80.

A process employing pullulanase is described by Hurst in U.S. Pat. No. 3,897,305. Isoamylase, whose use forms the subject matter of this invention is given but passing mention in U.S. Pat. No. 3,897,305. However, Allen et al. and numerous patents such as for example, U.S. Pat. Nos. 3,677,896 and 3,922,196 recommend employment of isoamylase together with a maltogenic beta-amylase in saccharifications when the objective is a high maltose content syrup.

Employment of pullulanase together with glucoamylase during saccharification of a 30% or more concentrated syrup will increase the DX value by 1-2%, but there are certain disadvantages when using pullulanase. The saccharification is usually conducted at a pH where the glucoamylase is only 60-30% active (e.g., about pH 5.5-6.0) whereas saccharification with glucoamylase alone is carried out at significantly lower pH levels, e.g., pH 4.0.

It has now been found that acidophilic isoamylases, such as *Pseudomonas amyloderamosa* isoamylase, which has a pH optimum of about 3.0-4.5, are almost ideal for combined use with glucoamylase during saccharification. Overall, one major result of the pH match is that the dose of glucoamylase can be reduced considerably, and a syrup with higher DX may be produced than is attainable with glucoamylase alone.

BRIEF STATEMENT OF THE INVENTION

According to practice of this invention maltodextrin solutions for example, starch hydrolysates of 8-12 DE, are saccharified by a combination of glucoamylase and isoamylase (EC3.2.1.68) at a pH below about 5, the preferred pH range being pH 3-5, at temperatures of 50° C.–60° C.

The glucoamylase dosage herein contemplated is significantly lower than industry has customarily used to make glucose syrups, being in the range of 0.05–0.3 AG units/g of DS (dry substance), preferably 0.075–0.15. The isoamylase dosage range is 25–500/IA units/g DS, preferably 100–200/IA units/g DS.

The reaction time is usually in the range of 24–96 hours, and the substrate concentrations contemplated are 20%–50% DS, preferably more than 30% of dry substance by wt.

DISCUSSION OF THE INVENTION

To facilitate understanding of this invention the analytical methods underlying the ranges provided above and the exemplary material provided hereinafter are outlined below.

GLUCOAMYLASE ACTIVITY

One AG unit of glucoamylase activity is the amount of enzyme which hydrolyses one micromole of maltose per minute at 25° C. and pH 4.3. A commercially available liquid form of glucoamylase from *Aspergillus niger* (Amyloglucosidase Novo 150, Novo Industri A/S, Denmark) contains 150 AG units per ml.

ISOAMYLASE ACTIVITY

One IA unit of isoamylase activity is the amount of enzyme which causes an increase in absorbency of 0.01 at 610 nm under the following standard conditions:

A reaction mixture consisting of 1 ml of a suitably diluted enzyme solution, 5 ml of 1% amylopectin (waxy-maize starch—SNOWFLAKE 04201—CPC) solution, and 1 ml of 0.5 M acetate buffer solution pH 3.5 is incubated at 40° C. for 30 minutes.

0.5 ml of the reaction mixture is withdrawn and mixed with 0.5 ml of 0.01 M iodine solution and 15 ml of 0.02 N $H_2SO_4$ solution. After 15 minutes the absorbency at a wavelength of 610 nm is determined.

An experimental isoamylase preparation from *Pseudomonas amyloderamosa* (Hayashibara, Japan) contained 500,000 IA units per gram.

PULLULANASE ACTIVITY

Pullulanase is assayed according to the CPC procedure described in British Pat. No. 1,144,950. One CPC unit is defined as the amount of enzyme required to produce 180 micrograms of reducing sugar, calculated as dextrose, per minute.

A commercially available pullulanase from *Klebsiella pneumoniae* PULLUZYME® S 2000 (ABM, UK) contained 3500 CPC units per gram.

DETERMINATION OF DEXTROSE (D-GLUCOSE)

Dextrose (D-Glucose) is determined by liquid chromatography (HPLC) according to the methods of Scobell et al., *Cereal Chemistry* 54 (4), July-August 1977, pages 905-917, and Engel and Olinger, *J. Assoc. Off. Anal. Chem.*, 62 (3) 1979), pp. 527-532.

DEXTROSE EQUIVALENT (DE)

Dextrose equivalent is determined according to CRA (Corn Refiner's Association), Method E 26.

As is well known in the art, the maximum DX value obtainable when saccharifying dextrin solutions is dependent upon the concentration of substrate in the solution. However, saccharifying relatively dilute solutions so as to improve DX is normally undesirable due to the expense of concentrating the (higher) DX syrup to whatever concentrations are wanted for later processing, or use, or shipping, whatever. Accordingly, the advantages offered by practice of this invention can be set out by a comparison based upon the DX results upon saccharification of starch hydrolysates at varying concentration in DS (dry substance) by wt.

Through practice of this invention 98% DX syrups can be obtained with a 25% DS dextrin. When saccharifying with glucoamylase alone (the conventional process) 98% DX cannot be obtained at higher than about 18% DS. Syrups of 96% DX are obtainable at solids level of 42% DS, as compared to 32% DS in the conventional process. Since starch can be liquefied into 35-45% DS solutions, the 96 DX syrups heretofore accepted by the art may be obtained directly from the concentrated starch hydrolysates potentially available to the art (without dilution thereof), offering to the art a reduction in reactor volumes per ton of dry solids saccharified per day, and a reduction in evaporation costs that accrue whenever reconcentration of saccharified starch hydrolysates are necessary.

Although the inventor herein has not fully compared the pullulanase/glucoamylase system suggested by U.S. Pat. No. 3,897,305 with the isoamylase/glucoamylase system of the present invention, enough has been done to ascertain that the DX improvement pointed out above is obtainable with pullulanase, and to believe that some, if not all, of the above described advantages over glucoamylase alone may apply as well. However, as has already been pointed out, the improvement obtainable with a pullulanase comes at the expense of a need to operate at pH levels (pH 5-6) that are not optimum for the glucoamylase. An advantage unique to the isoamylase/glucoamylase system is that the saccharification, e.g., to 96 DX, can be carried out at lowered glucoamylase dosage levels.

Referring now to the drawing wherein:

FIG. 1 is a graph of the relative activity versus pH for glucoamylase, isoamylase (from *Pseudomonas amyloderamosa*) and pullulanase; and FIG. 2 is a graph illustrating the maximum DX obtainable at various substrate concentrations for glucoamylase alone, and for a glucoamylase-isoamylase combination.

Illustrated in FIG. 2 is the variation in maximum DX with substrate concentration for a standard saccharification (Curve A), and for saccharification (Curve B) with ⅓ the dosage of glucoamylase augmented by 200 units of isoamylase per g of dry substance, the data being taken from Example 5 hereinafter provided.

The preferred isoamylase for practice of this invention is the isoamylase of *Pseudomonas amyloderamosa*. The optimum pH activity for this enzyme is in the range pH 3.0-4.5. This particular enzyme is, unfortunately, somewhat thermolabile, and best saccharification results with this isoamylase have been obtained at the lower end of the 50° C.-60° C. temperature range employed for the saccharification. The extent to which the pH optimum of this isoamylase is almost ideal for use with commercially available glucoamylase can be seen from FIG. 1.

Although the glucoamylase that converts starch in solution has been discussed and is hereinafter exemplified by a commercially available glucoamylase from one microorganism source, *Aspergillus niger*, which is the preferred glucoamylase, it should be appreciated that a great many genera of microorganisms contain species known to produce a glucoamylase. It should be appreciated that use of any and all glucoamylases fall within the scope of this invention. Parenthetically, it is noted that microorganisms capable of consuming starch are ubiquitous.

Although isoamylases have not been as well explored by the art as glucoamylases, numerous microorganism sources of isoamylase are known. See for example, the discussion of isoamylase by Allen et al. in *Food Technology*, May 1975, pp. 70-80. It should be appreciated that use of any and all isoamylases fall within the scope of this invention.

For further understanding of this invention, the following specific examples of practice thereof are presented.

EXAMPLE 1

100 kg of corn starch (Globe® 03430, CPC) were slurried with tap water containing 100 ppm $Ca^{++}$ and the volume adjusted to 225 liters. The pH was adjusted to 6.3 and 135 g of TERMAMYL® 60 L (NOVO Industri A/S, Denmark)—a thermostable alpha-amylase from *Bacillus licheniformis*—were added.

This suspension was continuously pumped through a jet cooker (Hydro-Thermal Corp. Milwaukee) where it was heated to 105° C. by direct steam injection and maintained at 105° C. for five minutes. The liquefied starch suspension was flash-cooled and pumped over into a saccharification tank where it was held for 1 hour at 95° C.

The pH of the liquefied starch was adjusted to 4.5 at 95° C. to stop the reaction and the batch was then spray-dried without purification. The DE of the spray-dried maltodextrin was 11.

Substrates for saccharification were prepared by redissolving suitable amounts of this maltodextrin in deionized water and making up to approximately 30% DS. Aliquots of this substrate were then taken and heated to 50° C. and the pH adjusted to 4.0. Different amounts of glucoamylase (Amyloglucosidase Novo 150) and Pseudomonas isoamylase were then added. The reaction mixtures were sampled at set time intervals and the % dextrose in each sample determined by HPLC. The following results were obtained:

| Glucoamylase AG units/ g DS | Isoamylase IA units/ g DS | DS % w/w | pH | Reaction time hours | DX % |
|---|---|---|---|---|---|
| 0.225 | 0 | 30 | 3.9 | 48 | 94.9 |
| 0.225 | 0 | 30 | 3.9 | 96 | 96.1 |
| 0.225 | 160 | 30 | 3.9 | 48 | 97.4 |
| 0.225 | 320 | 30 | 3.9 | 48 | 97.6 |
| 0.175 | 0 | 30 | 3.9 | 72 | 95.6 |
| 0.175 | 0 | 30 | 3.9 | 96 | 96.2 |
| 0.175 | 10 | 30 | 3.9 | 72 | 96.5 |
| 0.175 | 50 | 30 | 3.9 | 72 | 97.1 |
| 0.175 | 100 | 30 | 3.9 | 72 | 97.2 |

-continued

| Glucoamylase AG units/ g DS | Isoamylase IA units/ g DS | DS % w/w | pH | Reaction time hours | DX % |
|---|---|---|---|---|---|
| 0.175 | 200 | 30 | 3.9 | 72 | 97.5 |
| 0.150 | 100 | 30 | 3.9 | 48 | 97.0 |
| 0.150 | 200 | 30 | 3.9 | 48 | 97.4 |
| 0.150 | 400 | 30 | 3.9 | 48 | 97.8 |
| 0.075 | 100 | 30 | 3.9 | 96 | 97.2 |
| 0.075 | 150 | 30 | 3.9 | 96 | 97.6 |
| 0.075 | 200 | 30 | 3.9 | 96 | 97.6 |

These results indicate that when glucoamylase and isoamylase are used together the glucoamylase dosage can be reduced from 0.225 AG units/gram DS to 0.075 AG units/gram DS. At the same time the DX value can be increased by 1.5%.

EXAMPLE 2

Aliquots of the substrate prepared as in example 1 were heated to 55° or 60° C. and the pH adjusted to either 4.5 or 6.0. An amount of glucoamylase corresponding to 0.225 AG units per gram DS was added, followed by different amounts of pullulanase (PULLUZYME ® S 2000). The reaction mixtures were sampled and analysed as in example 1.

The following results were obtained:

| Glucoamylase AG units/ g DS | Pullulanase CPC units/ g DS | Temperature °C. | DS % w/w | Initial pH | Reaction time (hours) | pH | DX % |
|---|---|---|---|---|---|---|---|
| 0.225 | 0 | 60 | 30 | 4.5 | 48 | 4.2 | 96.0 |
| 0.225 | 0 | 60 | 30 | 4.5 | 72 | 4.2 | 96.4 |
| 0.225 | 0 | 55 | 31 | 4.5 | 48 | 4.4 | 96.0 |
| 0.225 | 0 | 55 | 31 | 4.5 | 72 | 4.3 | 96.4 |
| 0.225 | 1.3 | 55 | 30 | 6.0 | 48 | 5.2 | 96.5 |
| 0.225 | 1.3 | 55 | 30 | 6.0 | 72 | 5.2 | 96.9 |
| 0.225 | 2.6 | 55 | 30 | 6.0 | 48 | 5.3 | 97.3 |
| 0.225 | 2.6 | 55 | 30 | 6.0 | 72 | 5.2 | 97.6 |

These results indicate that DX values similar to those of example 1 can be obtained when using pullulanase and glucoamylase together. However, because saccharification takes place at pH 5.0–6.0 a high glucoamylase dosage is required.

EXAMPLE 3

Aliquots of the substrate prepared as in example 1 were incubated at 50°, 55° and 60° C. at pH 3.5 and 4.0. Different amounts of glucoamylase and isoamylase were added and the reaction mixtures sampled and analysed as in example 1. The following results were obtained:

| Glucoamylase AG units/ g DS | Isoamylase IA units/ g DS | DS % w/w | pH | Temperature °C. | Reaction time hours | DX % |
|---|---|---|---|---|---|---|
| 0.075 | 200 | 30 | 3.4 | 50 | 96 | 97.6 |
| 0.075 | 200 | 30 | 3.4 | 55 | 96 | 97.3 |
| 0.075 | 200 | 30 | 3.4 | 60 | 96 | 92.8 |
| 0.175 | 200 | 30 | 3.9 | 50 | 48 | 97.5 |
| 0.175 | 200 | 30 | 3.9 | 55 | 48 | 97.3 |
| 0.175 | 200 | 30 | 3.9 | 60 | 48 | 96.7 |
| 0.075 | 100 | 30 | 3.8 | 50 | 96 | 97.2 |
| 0.075 | 100 | 30 | 3.7 | 55 | 96 | 97.2 |
| 0.075 | 150 | 30 | 3.7 | 50 | 96 | 97.6 |
| 0.075 | 150 | 30 | 3.7 | 55 | 96 | 97.5 |
| 0.075 | 200 | 30 | 3.8 | 50 | 96 | 97.6 |
| 0.075 | 200 | 30 | 3.7 | 55 | 96 | 97.5 |
| 0.150 | 100 | 30 | 3.8 | 50 | 72 | 97.2 |
| 0.150 | 100 | 30 | 3.7 | 55 | 72 | 97.0 |
| 0.150 | 150 | 30 | 3.8 | 50 | 72 | 97.4 |
| 0.150 | 150 | 30 | 3.7 | 55 | 72 | 97.2 |
| 0.150 | 200 | 30 | 3.8 | 50 | 72 | 97.3 |
| 0.150 | 200 | 30 | 3.7 | 55 | 72 | 97.2 |

These data show that the best results are obtained when operating at 50°–55° C.

EXAMPLE 4

Aliquots of the substrate prepared as in example 1 were incubated at different pH values at 50° C. 0.075 AG units of glucoamylase and 200 IA units of isoamylase were added per gram DS. The reaction mixtures were sampled at set time intervals and analysed as in example 1. The following results were obtained:

| DS % w/w | pH | Reaction time (hours) | DX % |
|---|---|---|---|
| 30 | 3.0 | 24 | 56.6 |
| 30 | 2.9 | 48 | 81.8 |
| 30 | 2.9 | 72 | 92.4 |
| 30 | 2.9 | 96 | 95.4 |
| 30 | 3.5 | 24 | 58.4 |
| 30 | 3.4 | 48 | 85.9 |
| 30 | 3.4 | 72 | 96.2 |
| 30 | 3.4 | 96 | 97.6 |
| 30 | 3.9 | 24 | 60.0 |
| 30 | 3.9 | 48 | 87.5 |
| 30 | 3.9 | 72 | 96.5 |
| 30 | 3.9 | 96 | 97.7 |

These results show that saccharification may be carried out under mildly acidic conditions, i.e. at a pH below 4.0.

EXAMPLE 5

Substrates with different dry solids contents were prepared by dissolving 100 g of the DE 11 maltodextrin from example 1 in different amounts of deionized water. In a control saccharification at 60° C. the pH was adjusted to 4.5 and 0.225 AG units of glucoamylase added per gram DS. In the isoamylase saccharifications at 50° C. the pH was adjusted to 4.0 and 0.075 AG units of glucoamylase and 200 IA units of isoamylase were added per gram DS. The reaction mixtures were sampled and analysed as in example 1. The following results were obtained:

| Glucoamylase AG/g DS | Isoamylase IA/g DS | DS % w/w | Temp. °C. | pH | Maximum DX % |
|---|---|---|---|---|---|
| 0.225 | 0 | 20 | 60 | 4.2 | 97.8 |
| 0.225 | 0 | 25 | 60 | 4.2 | 97.2 |
| 0.225 | 0 | 30 | 60 | 4.1 | 96.4 |
| 0.225 | 0 | 35 | 60 | 4.1 | 95.5 |
| 0.225 | 0 | 40 | 60 | 4.0 | 94.4 |
| 0.225 | 0 | 45 | 60 | 4.0 | 93.2 |
| 0.075 | 200 | 20 | 50 | 3.9 | 98.4 |
| 0.075 | 200 | 25 | 50 | 3.8 | 98.0 |
| 0.075 | 200 | 30 | 50 | 3.8 | 97.5 |
| 0.075 | 200 | 35 | 50 | 3.8 | 97.0 |
| 0.075 | 200 | 40 | 50 | 3.7 | 96.4 |

-continued

| Gluco-amylase AG/g DS | Isoamylase IA/g DS | DS % w/w | Temp. °C. | pH | Maximum DX % |
|---|---|---|---|---|---|
| 0.075 | 200 | 45 | 50 | 3.7 | 95.6 |

The maximum obtainable DX values may be increased by carrying out saccharification at lower solids levels. When using the combination glucoamylase/isoamylase a DX value of 98 can be obtained when saccharifying at 25% DS. In order to achieve this level without isoamylase, saccharification has to take place at about 18% DS.

EXAMPLE 6

A further batch of maltodextrin substrate was prepared as in example 1. After 1 hour at 90° C. the pH was adjusted to 4.5 and the batch was spray-dried. The DE was found to be 8.0.

Substrates for saccharification were prepared by redissolving suitable amounts of maltodextrin in deionized water and adjusting the solids content to approximately 30% DS.

Aliquots of the reconstituted DE 8 maltodextrin were heated to 50° and 55° C. and the pH adjusted to 4.0. 200 IA units of isoamylase and 0.113 AG units of glucoamylase were added per gram DS. The reaction mixtures were sampled at regular intervals and the dextrose content determined by HPLC. The following results were obtained:

| Temp. °C. | DS % w/w | pH | Reaction time (hours) | DX % |
|---|---|---|---|---|
| 50 | 30 | 3.9 | 24 | 79.8 |
| 50 | 30 | 3.9 | 48 | 97.0 |
| 50 | 30 | 3.9 | 72 | 97.9 |
| 50 | 30 | 3.8 | 96 | 97.6 |
| 55 | 30 | 3.9 | 24 | 89.8 |
| 55 | 30 | 3.8 | 48 | 97.7 |
| 55 | 30 | 3.8 | 72 | 97.7 |
| 55 | 30 | 3.8 | 96 | 97.4 |

The results obtained with the DE8 maltodextrin indicate that the DX values obtained at 55° C. are similar to those obtained at 50° C.

EXAMPLE 7

Substrates with different dry solids contents were prepared by dissolving 100 grams of the DE 8 maltodextrin from example 6 in different amounts of deionized water. In the control saccharifications at 55° and 60° C. the pH was adjusted to 4.5 and 0.225 AG units of glucoamylase were added per gram DS. In the isoamylase saccharification at 55° C. the pH was adjusted to 4.0 and 0.112 AG units of glucoamylase activity and 200 IA units of isoamylase activity per gram DS were added. The reaction mixtures were sampled and analysed as in example 1. The following results were obtained:

| Gluco-amylase AG/g DS | Isoamylase IA/g DS | DS % w/w | Temp. °C. | pH | Maximum DX % |
|---|---|---|---|---|---|
| 0.225 | 0 | 20 | 60 | 4.0 | 97.7 |
| 0.225 | 0 | 25 | 60 | 4.0 | 97.2 |
| 0.225 | 0 | 30 | 60 | 4.0 | 96.4 |
| 0.225 | 0 | 35 | 60 | 4.0 | 95.5 |
| 0.225 | 0 | 40 | 60 | 4.0 | 94.3 |
| 0.225 | 0 | 45 | 60 | 4.0 | 93.0 |
| 0.225 | 0 | 20 | 55 | 4.2 | 97.9 |
| 0.225 | 0 | 25 | 55 | 4.2 | 97.4 |
| 0.225 | 0 | 30 | 55 | 4.2 | 96.6 |
| 0.225 | 0 | 35 | 55 | 4.2 | 95.7 |
| 0.225 | 0 | 40 | 55 | 4.2 | 94.5 |
| 0.225 | 0 | 45 | 55 | 4.2 | 93.2 |
| 0.112 | 200 | 20 | 55 | 3.9 | 98.6 |
| 0.112 | 200 | 25 | 55 | 3.8 | 98.2 |
| 0.112 | 200 | 30 | 55 | 3.8 | 97.6 |
| 0.112 | 200 | 35 | 55 | 3.8 | 96.9 |
| 0.112 | 200 | 40 | 55 | 3.7 | 96.1 |
| 0.112 | 200 | 45 | 55 | 3.7 | 95.2 |

The results obtained here with the DE8 maltodextrin are similar to those given in example 5.

I claim:

1. In a process for saccharifying a starch hydrolysate to a high DX glucose syrup with glucoamylase, the improvement which comprises saccharifying at pH 3–5 in the presence of an enzyme mixture comprising effective amounts of glucoamylase and an acidophilic isoamylase to convert the starch hydrolysate to at least about 96 DX glucose syrup, the glucoamylase dosage being in the range of 0.05–0.15 AG units per gram of dry substance in the hydrolysate.

2. The process of claim 1 wherein the solids content in the starch hydrolysate exceeds about 30% by weight.

3. The process of claim 1 wherein the saccharifying temperature is in the range of 50° C.–60° C.

4. The process of claim 1 wherein the saccharifying reaction is carried out for 24–96 hours.

5. The process of claim 1 wherein the isoamylase dosage is in the range of 25–500 IA units per gram of dry substance in the hydrolysate.

6. The process of claim 1 wherein the glucoamylase dosage is in the range of 0.075–0.15 AG units and the isoamylase dosage is in the range of 100–200 IA units, each being per gram of dry substance in the hydrolysate.

7. The process of claim 1 wherein the isoamylase is from *Pseudomonas amyloderamosa*.

8. The process of claim 7 wherein the glucoamylase is from *Aspergillus niger*.

* * * * *